United States Patent [19]

Rasheed et al.

[11] 4,240,821
[45] Dec. 23, 1980

[54] BIOCIDALLY-ACTIVE 1,3-BENZODITHIOLE-2-THIONE COMPOUNDS

[75] Inventors: Khalid Rasheed, Weslaco; James D. Warkentin, McAllen, both of Tex.

[73] Assignee: Ciba-Geigy Corporation, Ardsley, N.Y.

[21] Appl. No.: 92,464

[22] Filed: Nov. 8, 1979

Related U.S. Application Data

[60] Division of Ser. No. 821,977, Aug. 4, 1977, Pat. No. 4,187,096, which is a continuation-in-part of Ser. No. 618,255, Sep. 30, 1975, Pat. No. 4,084,954.

[51] Int. Cl.$^3$ .................. A01N 43/28; A61K 31/385; C07D 409/02
[52] U.S. Cl. .................. 71/90; 424/248.5; 424/250; 424/267; 424/274; 424/277; 260/326.82; 260/455 B; 544/145; 544/377; 546/197; 549/33
[58] Field of Search .................. 71/90; 424/277, 248.5, 424/250, 267, 274; 260/326.82; 544/145, 377; 546/197; 549/33

[56] References Cited

U.S. PATENT DOCUMENTS

| | | | |
|---|---|---|---|
| 3,214,442 | 10/1965 | Klingsberg | 549/33 |
| 3,444,186 | 5/1969 | Sakai et al. | 549/33 |
| 3,445,480 | 5/1969 | Allais et al. | 549/33 |
| 3,455,952 | 7/1969 | Bulbenko et al. | 549/33 |
| 3,491,119 | 1/1970 | Fields | 549/33 |
| 3,749,736 | 7/1973 | Diekman | 549/33 |
| 3,818,041 | 6/1974 | Fields | 549/33 |
| 4,084,954 | 4/1978 | Rasheed et al. | 71/90 |
| 4,139,362 | 2/1979 | Rasheed et al. | 71/90 |
| 4,175,186 | 11/1979 | Rasheed et al. | 544/145 |
| 4,187,096 | 2/1980 | Rasheed et al. | 544/158 X |

FOREIGN PATENT DOCUMENTS

| | | | |
|---|---|---|---|
| 1114506 | 10/1961 | Fed. Rep. of Germany | 549/33 |
| 823251 | 11/1959 | United Kingdom | 549/33 |

OTHER PUBLICATIONS

Hurtley, et al., J. Chem. Soc. 1926, pp. 1821 to 1828.
Hunig, et al., Annalen der Chemie, vol. 738, pp. 192 to 194, (1970).
Dallacker, et al., Chem. Ber., vol. 89, pp. 179 to 183, (1965).
Breslow, et al., "Multi- Sulfur and Sulfur and Oxygen Five- and Six-Membered Heterocycles, Part 1, pp. 475 and 564, Interscience Publishers, N.Y. (1966).
Shasha, et al., Nature, vol. 210, #5031, pp. 89-90, (1966).
Wizinger, et al., Helv. Chim. Acta, vol. 46, pp. 2167-2177, (1963).

*Primary Examiner*—John D. Randolph
*Attorney, Agent, or Firm*—Morgan, Finnegan, Pine, Foley & Lee

[57] ABSTRACT

1,3-Benzodithiole-2-thione compounds are disclosed including the novel method of preparing said compounds and their biocidal activity.

31 Claims, No Drawings

BIOCIDALLY-ACTIVE 1,3-BENZODITHIOLE-2-THIONE COMPOUNDS

CROSS-REFERENCE TO RELATED APPLICATIONS

This application is a division of application Ser. No. 821,977, filed Aug. 4, 1977, now U.S. Pat. No. 4,187,096, issued Feb. 5, 1980, which in turn is a continuation-in-part of application Ser. No. 618,255, filed Sept. 30, 1975, now U.S. Pat. No. 4,084,954, issued Apr. 18, 1978.

BACKGROUND OF THE INVENTION

This invention relates generally to new and useful biocidally active compounds. More specifically, it relates to novel 1,3-benzodithiole-2-thione compounds prepared by an unusual but highly simple and convenient cyclization reaction. In fact, it is due to this synthesis that the numerous derivatives disclosed herein can be obtained so easily and in good yields.

The novel compounds of this invention are useful in treating pests such as fungi, insects and mites associated with growing plants in order to beneficially enhance the growth and/or yield-potential of said growing plants. This is accomplished by applying a biocidally active amount of the subject compound to the growing plant.

For purposes of this disclosure and for the sake of convenience and clarity, certain terms used herein are defined as follows:

The phrase "treating fungi, insects and mites associated with growing plants" signifies the application of a compound as herein defined to combat fungi, insects and mites associated with growing plants which embraces germinating plants, e.g. sprouts, seedlings, and fully grown plants. The mode of application will depend on the desired end use.

When treatment comprises foliar fungicidal, insecticidal or miticidal application, the compound is administered, as a spray, directly onto the leaves and other above ground portions of diseased plants.

All of the aforesaid treatments, whatever the objective, have a unitary result. That is, they beneficially enhance or improve the growth and/or yield potential of the treated plant.

The term "biocidally active amount" means an amount of compound which effectively permits the desired objective.

SUMMARY OF THE INVENTION

Accordingly, this invention is concerned with compounds of the formulae:

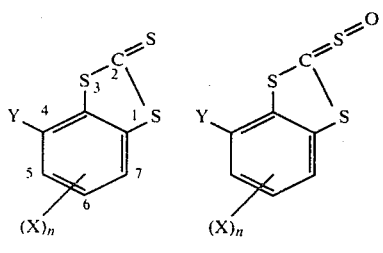

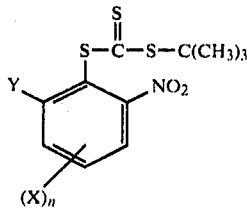

wherein Y is selected from hydrogen, cyano, alkylsulfonyl, nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, N-morpholino, N-piperidino, N-piperazino, N-pyrrolidino, dimethylaminodithiocarbamyl, carboalkoxy, alkythio, mono- and dialkylamino, N-alkylcarbamyl, N,N-dialkylcarbamyl, alkylsulfoxy, alkyl sulfonyl, said alkyl groups containing from 1 to 4 carbon atoms; n is an integer from 0 to 3; and salts thereof.

Of particular interest are compounds as shown having formula I above wherein Y is nitro and n is 1, such as:

4-nitro-6-trifluoromethyl-1,3-benzodithiole-2-thione and wherein Y is trifluoromethyl and n is 1, e.g.

5-nitro-7-trifluoromethyl-1,3-benzodithiole-2-thione.

Others which are preferred are those as shown above having formula I wherein Y is trifluoromethyl and n is 2 such as:

4-diethylamino-5-nitro-7-trifluoromethyl-1,3-benzodithiole-2-thione 4-dimethylamino-5-nitro-7-trifluoromethyl-1,3-benzodithiole-2-thione.

Also within the purview of this invention is the novel process for preparing such compounds involving a unique cyclization step as well as the use of such compounds to beneficially enhance the growth and/or yield-potential of plants.

DETAILED DESCRIPTION OF THE INVENTION

The novel compounds of this invention having formula I are prepared by a novel procedure wherein a unique cyclization step is involved. It is this synthetic method which allows for the formation of the numerous compounds disclosed herein. Compounds which would ordinarily be inaccessible or at best, tedious and difficult to make, are rendered available by an unusually simple and mild synthesis.

The process can be expressed by the following reactions:

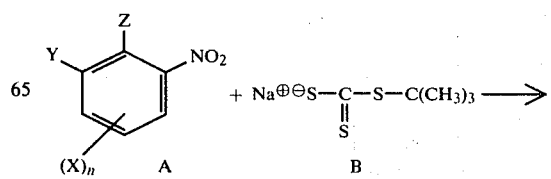

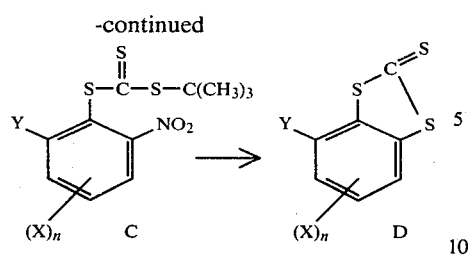

wherein Y is selected from hydrogen, cyano, alkylsulfonyl, nitro and tirfluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, N-morpholino, N-piperidino, N-piperazino, N-pyrrolidino, dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms and n is an integer from 0 to 3; Z is halogen (F, Cl, Br, I) or alkoxy, and R and R' are each alkyl groups straight- or branch-chained, containing from 1 to 4 carbon atoms.

Starting material A is typically a halobenzene derivative, many of which are commercially available. If not, one can easily synthesize the desired compound using well-documented chemical techniques. As is apparent, the halo group (Z) and the adjacent nitro group both undergo substitution thereby effecting cyclization to form the heterocyclic 5-membered ring. The other reagent, B, is S-tertiarybutyl sodium trithiocarbonate.

The attractiveness of the above process is that under relatively mild conditions, using generally available or easily accessible reagents, one can obtain the desired compounds in good yields. The intermediate product C of this reaction is usually isolated. However, it is possible to effect cyclization directly, to produce final product D, the substituted 1,3-benzodithiole-2-thiones.

The novelty of this synthetic method is clearly evident so one skilled in the art. It enables one to fuse onto a benzene ring containing adjacent nitro and halo groups a cyclic ring having the structure:

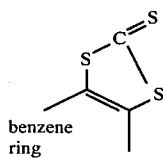

Importantly, it allows one to do this under mild conditions and using various chlorobenzene derivatives so that almost any desired substituted compound results.

The first step in reaction process is carried out in the temperature range of from $-10°$ C. to $200°$ C. In many instances, the reaction proceeds at room temperature or lower, whereas, in some cases, elevated temperatures may be desired in order to accelerate the reaction.

The reaction is usually carried out in a solvent, although the solvent may be omitted if effective dissolution of materials is possible. A solvent is generally preferred, however, and it can be any solvent which does not enter into the reaction and in which the reactants are soluble to some extent. Suitable solvents are dimethylformamide, dimethylsulfoxide, acetone and methyl isobutyl ketone.

The mole ratio of reagents A and B is normally 1 to 1, however, it is generally preferred to use a slight excess of reagent B to ensure more complete reaction.

Intermediate C can be isolated prior to conversion to product D or it can be decomposed directly. If isolated, the decomposition of C to D is typically effected in a solvent such as ethanol, acetone, dimethyl sulfoxide or glacial acetic acid. If decomposition is effected directly, the reaction mixture containing intermediate C is treated to produce product D.

The aforesaid decomposition reaction is accomplished generally by a heating step at temperatures in the range from $20°$ C. to $200°$ C. In certain instances, that decomposition will occur at lower temperatures without the need for a heating step.

The work-up is standard—product is obtained by precipitation, washing, drying and recrystallization if necessary.

Product D can be further reacted under peroxidation conditions to provide trithione oxides E as follows:

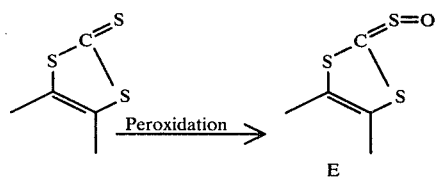

This reaction is effected under standard peroxidation conditions using any suitable peroxide catalyst, e.g. peracetic acid.

The biocidal processes of this invention comprise applying a biocidally effective amount of a compound disclosed herein to growing plants. The compounds are formulated for use either as sprays made up by adding water to emulsifiable concentrates or wettable powders, as granules or as dispersions on carriers such as attapulgite clay granules, peat moss, fertilizer, vermiculite, etc. The compounds are quite insoluble in water, and hence, for the preparation of emulsions or wettable powders, the compounds are preferably formulated with wetting agents.

Since numerous compounds disclosed herein are free bases and acids, they can be converted to acid salts (free bases) and base salts (free acids).

The acid-addition and base-addition salts are within the purview of this invention. The acid-addition salts are easily prepared by treating the amine base with a substantially equimolar amount of a chosen acid in an aqueous solution or in a suitable organic solvent such as methanol or ethanol. The only restriction on the acid used is that it provides acceptable ions, i.e., those which do not deleteriously affect the growing plants. The base-addition salts are prepared in a similar manner except that base instead of acid is added. The same restriction with respect to acceptable ions applies.

For foliar fungicidal, insecticidal and miticidal use, the compounds disclosed herein are applied at a rate of about 200 to 5000 parts per million as an emulsion in water.

EXAMPLE I

4-Nitro-6-trifluoromethyl-1,3-benzodithiole-2-thione

To a stirred and cooled (freezing mixture) solution of 27.0 g (0.1 mole) of 3,5-dinitro-4-chlorobenzotrifluoride (I) in 100 ml of acetone was added dropwise a solution of 24.7 g (0.11 mole) of S-tert.butyl sodium trithiocarbonate (II) in 150 ml of acetone. The temperature of the reaction mixture was maintained at −10° to −5° C. during addition of II. Mixture allowed to stir at room temperature overnight, poured into 1200 ml of water, and extracted with three 100 ml portions of methylene chloride. After drying over anhy. $Na_2SO_4$, the methylene chloride extract was freed of solvent by distilling in vac. on a rotary evaporator. The residual material was triturated with cold ethanol, suction filtered and dried. This yielded 16.0 g (40% theor.) of S-tert.butyl-S'-(2,6-dinitro-4-trifluoromethylphenyl)-trithiocarbonate (III).

15 g (0.037 mole) of III was dissolved in 125 ml of glacial acetic acid and heated to 90°–100° C. for 45 minutes. The mixture was poured into 500 ml of water, extracted with three 100 ml portions of methylene chloride. The organic extract was dried ($Na_2SO_4$) and solvent removed by distillation in vac. The residual solid was recrystallized from ethanol. There was obtained 6.0 g (55% theor.) of 4-nitro-6-trifluoromethyl-1,3-benzodithiole-2-thione, m.p. 163°–165° C. Analytical: Calcd. for $C_8H_2F_3NO_2S_3$: C, 32.32; H, 0.67; S, 32.32. Found: C, 32.18; H, 0.74; S, 32.21. Mass Spectrum mol. wt.=297. NMR($d_6$DMSO); 8.63δ(1H,m); 8.73(1H,m).

EXAMPLE II

The procedure of Example I is repeated wherein the following chlorobenzene derivatives are used in place of 2,6-dinitro-4-trifluoromethylchlorobenzene to provide the corresponding products:

| chlorobenzene derivative | Product |
| --- | --- |
| 2,6-dinitro-4-cyano-chlorobenzene | 4-nitro-6-cyano-1,3-benzodithiole-2-thione |
| 2,4-dinitro-3-dimethylamino-6-trifluoromethyl-chlorobenzene | 7-dimethylamino-6-nitro-4-trifluoromethyl-1,3-benzodithiole-2-thione |
| 2,4-dinitro-6-trifluoromethyl-chlorobenzene | 5-nitro-7-trifluoromethyl-1,3-benzodithiole-2-thione |
| 2,4-dinitro-3-diethylamino-6-trifluoromethyl-chlorobenzene | 7-diethylamino-6-nitro-4-trifluoromethyl-1,3-benzodithiole-2-thione |
| 2,6-dinitro-5-trifluoromethyl-chlorobenzene | 4-nitro-7-trifluoromethyl-1,3-benzodithiole-2-thione |
| 2,4-dinitro-3-monopropylamino-6-trifluoromethyl-chlorobenzene | 7-monopropylamino-6-nitro-4-trifluoromethyl-1,3-benzodithiole-2-thione |
| 2,4-dinitro-3-di-n-propylamino-6-trifluoromethyl-chlorobenzene | 7-di-n-propylamino-6-nitro-4-trifluoromethyl-1,3-benzodithiole-2-thione |
| 2,6-dinitro-4-methyl-chlorobenzene | 6-methyl-4-nitro-1,3-benzodithiole-2-thione |
| 2,4,6-trinitro-chlorobenzene | 4,6-dinitro-1,3-benzodithiole-2-thione |
| 2,6-dinitro-4-fluoro-chlorobenzene | 6-fluoro-4-nitro-1,3-benzodithiole-2-thione |
| 4-chloro-2,6-dinitro-chlorobenzene | 6-chloro-4-nitro-1,3-benzodithiole-2-thione |
| 2,4-dichloro-3-methyl-2,6-dinitro-chlorobenzene | 6-chloro-7-methyl-4-nitro-1,3-benzodithiole-2-thione |
| 3-chloro-2,6-dinitro-4-trifluoromethyl-chlorobenzene | 7-chloro-4-nitro-6-trifluoromethyl-1,3-benzodithiole-2-thione |
| 2,6-dinitro-chlorobenzene | 4-nitro-1,3-benzodithiole-2-thione |
| 3,5-dimethyl-2,4,6-trinitro-chlorobenzene | 5,7-dimethyl-4,6-dinitro-1,3-benzodithiole-2-thione |
| 3-di-n-propylamino-2,4-dinitro-6-trifluoromethyl-chlorobenzene | 7-di-n-propylamino-6-nitro-4-trifluoromethyl-1,3-benzodithiole-2-thione |
| 2,4-dinitro-3-monoisopropyl-amino-6-trifluoromethyl-chlorobenzene | 7-monoisopropylamino-6-nitro-4-trifluoromethyl-1,3-benzodithiole-2-thione |
| 2,4-dinitro-3-mono-n-propyl-amino-6-trifluoromethyl-chlorobenzene | 7-monopropylamino-6-nitro-4-trifluoromethyl-1,3-benzodithiole-2-thione |
| 3-diethylamino-2,4-dinitro-6-trifluoromethyl-chlorobenzene | 7-diethylamino-6-nitro-4-trifluoromethyl-1,3-benzodithiole-2-thione |
| 2,4-dinitro-3-n-propythio-6-trifluoromethyl-chlorobenzene | 6-nitro-7-n-propylthio-4-trifluoromethyl-1,3-benzodithiole-2-thione |
| 2,4-dinitro-3-isopropylthio-6-trifluoromethyl-chlorobenzene | 7-isopropylthio-6-nitro-4-trifluoromethyl-1,3-benzodithiole-2-thione |
| 4-cyano-2,6-dinitro-chlorobenzene | 6-cyano-4-nitro-1,3-benzodithiole-2-thione |
| 3-diallylamino-2,4-dinitro-6-trifluoromethyl-chlorobenzene | 7-diallylamino-6-nitro-4-trifluoromethyl-1,3-benzodithiole-2-thione |
| 2,4-dinitro-3-methylamino-6-trifluoromethyl-chlorobenzene | 7-methylamino-6-nitro-4-trifluoromethyl-1,3-benzodithiole-2-thione |
| 2,4-dinitro-3-monobutylamino-6-trifluoromethyl-chlorobenzene | 7-mono-n-butylamino-6-nitro-4-trifluoromethyl-1,3-benzodithiole-2-thione |
| 3-dibutylamino-2,4-dinitro-6-trifluoromethyl-chlorobenzene | 7-di-n-butylamino-6-nitro-4-trifluoromethyl-1,3-benzodithiole-2-thione |
| 2,4-dinitro-3-monophenylamino-6-trifluoromethyl-chlorobenzene | 7-monophenylamino-6-nitro-4-trifluoromethyl-1,3-benzodithiole-2-thione |
| 2,4-dinitro-3-piperidino-6-trifluoromethyl-chlorobenzene | 6-nitro-7-piperidino-4-trifluoromethyl-1,3-benzodithiole-2-thione |
| 2,4-dinitro-3-morpholino-6-trifluoromethyl-chlorobenzene | 7-morpholino-6-nitro-4-trifluoromethyl-1,3-benzodithiole-2-thione |
| 2,4-dinitro-3-pyrrolidino-6-trifluoromethyl-chlorobenzene | 6-nitro-7-pyrrolidino-4-trifluoromethyl-1,3-benzodithiole-2-thione |
| 2,4-dinitro-chlorobenzene | 5-nitro-1,3-benzodithole-2-thione |
| 2-nitro-4-trifluoromethyl-chlorobenzene | 5-trifluoromethyl-1,3-benzodithiole-2-one |

In all instances, intermediate trithiocarbonate is first isolated.

EXAMPLE III

The procedure of Example I is repeated wherein the following solvents are used in place of acetone with comparable results:
dimethylsulfoxide
dimethylformamide
methylisobutyl ketone
glacial acetic acid

EXAMPLE IV

The procedure of Example I is repeated wherein the following halobenzene derivatives are used in place of 2,6-dinitro-4-trifluoromethyl-chlorobenzene to provide corresponding products:

| | | halobenzene derivative | | |
|---|---|---|---|---|
| Z | Y | $X_1$ | $X_2$ | $X_3$ |
| Cl | $NO_2$ | allyl | H | H |
| Br | $NO_2$ | hexyl | H | H |
| F | $NO_2$ | H | $CCl_3$ | H |
| Cl | $NO_2$ | H | $CF_3O$ | H |
| Cl | $CF_3$ | H | $CH_3SO_2$ | H |
| Cl | $NO_2$ | H | $CF_3S$ | H |
| Cl | $NO_2$ | H | $CF_3SO$ | H |
| Cl | $NO_2$ | H | CN | H |
| Cl | $NO_2$ | H | $CF_3SO_2$ | H |
| Cl | $NO_2$ | H | H | H |
| Cl | $NO_2$ | H | $CH_3OCH_2$ | H |
| Cl | $CF_3$ | H | CN | H |
| Cl | $CF_3$ | H | COOH | H |
| Cl | $CF_3$ | H | OH | H |
| Cl | $CF_3$ | H | $NH_2$ | H |

EXAMPLE V

For determination of foliar fungicidal activity for the herein disclosed compounds, the following screen was used.

Powdery Mildew of Cucumbers

Cucumber plants of a susceptible variety are grown in paper pots with 4 to 6 plants per pot. When the first leaves have reached a size of about two inches in diameter, they are sprayed with the test solutions (5000 PPM) with two pots used for each treatment applied. After the spraying treatments have dried thoroughly, the plants are dusted with spores of powdery mildew fungus, *Erysiphe cichoracearum*, reared on cucumber plants. Observations are made for disease symptoms throughout a period of 15 days.

The following compounds exhibited foliar fungicidal properties:
 4-nitro-6-trifluoromethyl-1,3-benzodithiole-2-thione
 4-dimethylamino-5-nitro-7-trifluoromethyl-1,3-benzodithiole-2-thione
 5-nitro-7-trifluoromethyl-1,3-benzodithiole-2-thione
 4-diethylamino-5-nitro-7-trifluoromethyl-1,3-benzodithiole-2-thione.

The following intermediate showed foliar fungicidal activity:
 S-tert.butyl-S'-(2,4-dinitro-3-aminopropyl-6-trifluoromethylphenyl)-trithiocarbonate.

The following thione-oxides exhibited foliar fungicidal activity:
 4-aminopropyl-5-nitro-7-trifluoromethyl-1,3-benzodithiole-2-thione oxide
 4-dimethylamino-5-nitro-7-trifluoromethyl-1,3-benzodithiole-2-thione oxide.

EXAMPLE VI

For determination of insecticidal and miticidal activity, the following screens were used.

The samples are tested at 5000 PPM with the exception of the pea aphid systemic test where 100 PPM is utilized.

Houseflies

Fifty adult houseflies are sprayed in 2×5 inch diameter stainless steel cages faced on top and bottom with 14 mesh screen. The insects are retained in the same cages for knockdown observations after 2 hours. The 24 hour mortality may be from residual as well as from direct contact.

Southern Armyworm and Mexican Been Beetle

Lima bean leaves dipped into test solutions are offered to ten larvae of the Southern Armyworm (late third instar) and the Mexican Bean Beetle (late second instar). Mortality is recorded after a 48 hour feeding period.

Pea Aphid

Ten adult pea aphids are sprayed and transferred to sprayed pea plants and held for 48 hour mortality determinations.

Spider Mite

Excised lima bean plants are infested with 50 to 100 adults of the strawberry spider mite prior to testing. Adult mortality presence or absence of nymphs and phytotoxicity are noted.

Systemic Aphid Test

Systemic insecticidal activity is evaluated by applying 25 milliliters of the sample to the vermiculite substratum of potted pea seedlings. Three days after application, the pea plants are infested with ten adult aphids. Mortality determinations are made after 5 days.

The following compounds exhibited insecticidal and miticidal activity:
 4-nitro-6-trifluoromethyl-1,3-benzodithiole-2-thione
 4-dimethylamino-5-nitro-7-trifluoromethyl-1,3-benzodithiole-2-thione
 5-nitro-7-trifluoromethyl-1,3-benzodithiole-2-thione
 4-diethylamino-5-nitro-7-trifluoromethyl-1,3-benzodithiole-2-thione.

The following intermediate showed miticidal activity:
 S-tert.butyl-S'-(2,4-dinitro-3-aminopropyl-6-trifluoromethylphenyl)-trithiocarbonate.

The following thione oxides exhibited miticidal and insecticidal activity:
 4-aminopropyl-5-nitro-7-trifluoromethyl-1,3-benzodithiole-2-thione oxide
 4-nitro-6-trifluoromethyl-1,3-benzodithiole-2-thione oxide
 4-dimethylamino-5-nitro-7-trifluoromethyl-1,3-benzodithiole-2-thione oxide.

EXAMPLE VII

4-Nitro-6-trifluoromethyl-1,3-benzodithiole-2-thione oxide

To a stirred solution of 7.35 g., (24.7 mmoles) of 4-nitro-6-trifluoromethyl-1,3-benzodithiole-2-thione in 150 ml. of chloroform was added dropwise a solution of 5.17 g., (24.7 mmoles) of 40% peracetic acid in 50 ml. of chloroform over a period of 20 minutes, the temperature being maintained at 8°–12° C.

The reaction mixture was allowed to stir at ambient temperature for 30 minutes, the resulting solution washed with two 150 ml. portions of water, dried [$Na_2SO_4$] and the solvent distilled in vacuum.

The residual crystalline material was recrystallized from ethanol and yielded 4.18 g. [53%] of the thione oxide, MP 163° C. dec. NMR (d₆DMSO); 8.70δ[1H, M]; 8.45 [1H, M]. The mixed MP with starting material gave a depression of melting point.

It should be understood by those skilled in the art that various modifications may be made in the present invention without departing from the spirit and scope thereof as described in the specification and defined in the appended claims.

What is claimed is:

1. A compound selected from the group consisting of those of the formulae:

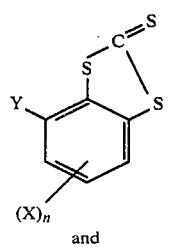

and

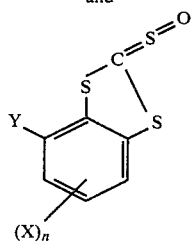

wherein Y is selected from nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, halogen (F, Cl, Br, I), hydroxy, acetylamino, amino, N-phenylamino, N,N-diallylamino, alkoxy, N-morpholino, N-piperidino, N-piperazino, N-pyrrolidino, dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms; n is an integer from 1 to 3 wherein at least one of said X groups is selected from N-morpholino, N-piperidino, N-piperazino or N-pyrrolidino; and salts thereof.

2. A compound as claimed in claim 1 of formula I wherein Y is nitro and n is 1.

3. A compound as claimed in claim 1 of formula I wherein Y is trifluoromethyl and n is 1.

4. A compound as claimed in claim 1 having formula I wherein Y is trifluoromethyl and n is 2.

5. A compound as claimed in claim 1 of formula II wherein Y is nitro and n is 1.

6. A compound as claimed in claim 1 of formula II wherein Y is CF₃ and n is 2.

7. A compound as claimed in claim 1 wherein Y is CF₃ and n is 2.

8. The compound as claimed in claim 7 which is S-tert.butyl-S'-(2,4-dinitro-3-aminopropyl-6-trifluoromethylphenyl)-trithiocarbonate.

9. A composition comprising a compound as claimed in claim 1 and an inert diluent therefor.

10. A process for preparing compounds of the formula:

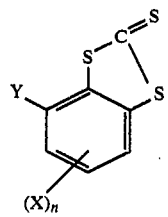

wherein Y is selected from hydrogen, cyano, alkylsulfonyl, nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, N-morpholino, N-piperidino, N-piperazino, N-pyrrolidino, dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms and n is an integer from 1 to 3 wherein at least one of said X groups is selected from N-morpholino, N-piperidino, N-piperazino or N-pyrrolidino which comprises reacting a nitrobenzene compound of the formula:

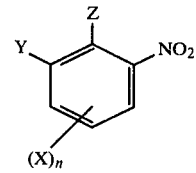

wherein Z is halogen (F, Cl, Br, I) or alkoxy, Y, X and n are as defined above;

with S-tertiarybutyl sodium trithiocarbonate to provide an intermediate, which intermediate is decomposed to provide the desired compound.

11. The process of claim 10 wherein said reaction is carried out in a solvent at a temperature in the range from −10° C. to 200° C.

12. The process of claim 10 wherein said intermediate is isolated prior to decomposition.

13. The process of claim 10 wherein said intermediate is decomposed by heating in a solvent at a temperature in the range from 20° C. to 200° C.

14. The process of claim 10 for preparing compounds having formula I wherein Y is nitro and n is 1 which comprises reacting a nitrohalobenzene of formula II wherein Y is nitro and n is 1 with said S-tertiarybutyl sodium trithiocarbonate, decomposing said intermediate and recovering product.

15. The process of claim 10 for preparing compounds having formula I wherein Y is CF₃ and n is 1 which comprises reacting a nitrohalobenzene of formula II wherein Y is CF₃ and n is 2 with said S-tertiarybutyl sodium trithiocarbonate, decomposing said intermediate and recovering product.

16. The process of claim 14 for preparing compounds having formula I wherein Y is trifluoromethyl and n is 2 which comprises reacting a nitrobenzene of formula II wherein Y is trifluoromethyl and n is 2 with said S-tertiarybutyl sodium trithiocarbonate and recovering product.

17. The product obtained by the process of claim 10.
18. A process for preparing compounds of the formula:

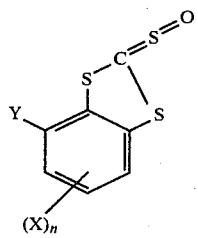

wherein Y is selected from hydrogen, cyano, alkylsulfonyl, nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, N-morpholino, N-piperidino, N-piperazino, N-pyrrolidino, dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms and n is an integer from 1 to 3 wherein at least one of said X groups is selected from N-morpholino, N-piperidino, N-piperazino or N-pyrrolidino which comprises subjecting a compound of the formula:

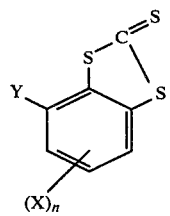

wherein Y, X and n are as defined above to peroxidation conditions.

19. A method of treating pests associated with growing plants selected from fungi, insects and mites to beneficially enhance the growth and/or yield-potential of said growing plants which comprises treating soil, seed or said plants with a biocidally active amount of a compound selected from the group consisting of those of the formulae: dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms; n is an integer from 1 to 3 wherein at least one of said X groups is selected from N-morpholino, N-piperidino, N-piperazino or N-pyrrolidino; and salts thereof.

20. The method as claimed in claim 19 wherein said compound has formula I as shown in claim 30 in which Y is nitro and n is 1.
21. The method as claimed in claim 19 wherein said compound has formula I as shown in claim 30 in which Y is CF$_3$ and n is 1.
22. The method as claimed in claim 19 wherein said compound has formula I as shown in claim 30 in which Y is trifluoromethyl and n is 2.

23. The method as claimed in claim 19 wherein said compound has formula II in which Y is nitro and n is 1.
24. The method as claimed in claim 19 wherein said compound has formula II in which Y is CF$_3$ and n is 2.
25. The method as claimed in claim 19 in which Y is CF$_3$ and n is 2.
26. The method as claimed in claim 25 in which the compound is S-tert. butyl-S'-(2,4-dinitro-3-aminopropyl-6-trifluoromethylphenyl)-trithiocarbonate.
27. The method of claim 19 wherein said compound is combined with an inert diluent.
28. A compound of the formula:

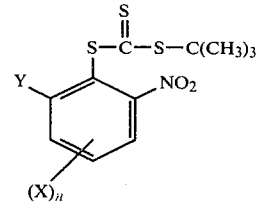

wherein Y is selected from nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, halogen (F, Cl, Br, I), hydroxy, acetylamino, amino, N-phenylamino, N,N-diallylamino, alkoxy, N-morpholino, N-piperidino, N-piperazino, N-pyrrolidino, dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms; n is an integer from 0 to 3; and salts thereof.

29. A composition comprising a compound as claimed in claim 28 and an inert diluent therefor.
30. A method of treating pests associated with growing plants selected from fungi, insects and mites to beneficially enhance the growth and/or yield-potential of said growing plants which comprises treating soil, seed or said plants with a biocidally active amount of a compound of the formula:

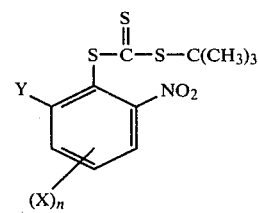

wherein Y is selected from hydrogen, cyano, alkylsulfonyl, nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, N-morpholino, N-piperidino, N-piperazino, N-pyrrolidino, dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms; n is an integer from 0 to 3; and salts thereof.

31. The method of claim 30 wherein said compound is combined with an inert diluent.

* * * * *